United States Patent [19]
Xu et al.

[11] Patent Number: 5,663,067
[45] Date of Patent: Sep. 2, 1997

[54] **METHOD FOR CLONING AND PRODUCING THE SAPI RESTRICTION ENDONUCLEASE IN *E. COLI***

[75] Inventors: Shuang-yong Xu, Lexington; Jian-ping Xiao, Wenham; Robert E. Maunus, Danvers, all of Mass.

[73] Assignee: New England Biolabs, Inc., Beverly, Mass.

[21] Appl. No.: 678,304

[22] Filed: Jul. 11, 1996

[51] Int. Cl.$^6$ ............ C12N 9/22; C12N 15/55; C12N 15/70
[52] U.S. Cl. ............ 435/199; 435/252.33; 435/320.1; 536/23.2
[58] Field of Search ............ 435/199, 320.1, 435/252.33; 536/23.2

[56] References Cited

U.S. PATENT DOCUMENTS

| | | | |
|---|---|---|---|
| 5,200,333 | 4/1993 | Wilson | 435/172.3 |
| 5,498,535 | 3/1996 | Fomenkov et al. | 435/172.3 |
| 5,532,153 | 7/1996 | Xu et al. | 435/199 |

OTHER PUBLICATIONS

Kosykh, et al., Molec. Gen. Genet. 178:717–718 (1980).
Mann, et al., Gene, 3:97–112 (1978).
Walder, et al., Proc. Nat. Acad. Sci., 78:1503–1507 (1981).
Bougueleret, et al., Nucl. Acid Res., 12:3659–3676 (1984).
Gingeras and Brooks, Proc. Nat. Acad. Sci., 80:402–406 (1983).
Theriault and Roy, Gene, 19:355–359 (1982).
Blumenthal, et al., J. Bacteriol., 164:501–509 (1985).
Kiss, et al., Nuc. Acid Res., 13:6403–6421 (1985).
Szomolanyi, et al., Gene, 10:219–225 (1980).
Janulaitis, et al., Gene,20:197–204 (1982).
Kiss and Baldauf, Gene, 21:111–119 (1983).
Walder, et al., J. Biol. Chem., 258:1235–1241 (1983).
Fomenkov, et al., Nuc. Acid Res. 22:2399–2403 (1994).
Raleigh and Wilson, Proc. Nat. Acad. Sci., 83:9070–9074 (1986).
Amann, Gene, 25:167–178 (1983).

*Primary Examiner*—Charles L. Patterson, Jr.
*Attorney, Agent, or Firm*—Gregory D. Williams

[57] ABSTRACT

The present invention relates to recombinant DNA which encodes the SapI restriction endonuclease and modification methylase, and the production of SapI restriction endonuclease from the recombinant DNA as well as to methods for cloning Actinomycetes genes into suitable hosts such as *E. coli*.

6 Claims, 5 Drawing Sheets

```
   1 GTGTTGGAAACTCTTGAGCTAGTCAACAAAATTGCGGAGTTTCAAAGGAAGCTACCTTAC
     M  L  E  T  L  E  L  V  N  K  I  A  E  F  Q  R  K  L  P  Y
  61 ACGCAGGACGACTATAAGAGTCGCTCCTGGGGGCACCCCTTGCACTCCCTTTGTTCGTAC
     T  Q  D  D  Y  K  S  R  S  W  G  H  P  L  H  S  L  C  S  Y
 121 CAGGGAAAGTTGAAACCTTCGCTTGCTCACTGGCTCGTTAAGACATTCTCGCCGGAAGGT
     Q  G  K  L  K  P  S  L  A  H  W  L  V  K  T  F  S  P  E  G
 181 GGCACGGTACTCGATCCGATGGGAGGCGTGGGAACAATAGCCTTTGAAGCGGCTCTAACG
     G  T  V  L  D  P  M  G  G  V  G  T  I  A  F  E  A  A  L  T
 241 GGTCGGGTCGGGATAACCAACGACAAAAGTCCATTGGCCGCTACTGTCACCGCCGGCAAG
     G  R  V  G  I  T  N  D  K  S  P  L  A  A  T  V  T  A  G  K
 301 CTTGCCCCGTCGTCTATACTGGAAGCTGAAGAGGCCATTGGTCGACTGGCGGAAGATATT
     L  A  P  S  S  I  L  E  A  E  E  A  I  G  R  L  A  E  D  I
 361 GAATCGGTGGACCTCAGTGCTGCAGATTATGAAGCCGCCAATTTCGGCTTGAATGCACGC
     E  S  V  D  L  S  A  A  D  Y  E  A  A  N  F  G  L  N  A  R
 421 GTTTCTGACTACTATCACCCGGATACTCTCAAAGAGATTTTGCGCGCGCGCCGTATTTTT
     V  S  D  Y  Y  H  P  D  T  L  K  E  I  L  R  A  R  R  I  F
 481 AGCGAGAGACGAGAAGCTTACCCAGCATTTGTCTGGGCATCTTTGTTGCATGTACTGCAT
     S  E  R  R  E  A  Y  P  A  F  V  W  A  S  L  L  H  V  L  H
 541 GGAAATCGGCCATATGCGTTGTCGCGGATTTCGCACCCAATTACACCTTTCAACCCGTCA
     G  N  R  P  Y  A  L  S  R  I  S  H  P  I  T  P  F  N  P  S
 601 GGGGTAGCtGAGTACAGATCGGTAGTCGAGAAGATTGCCCACCGcGCCCGGCTTGCTCTA
     G  V  A  E  Y  R  S  V  V  E  K  I  A  H  R  A  R  L  A  L
 661 AGGAATCCGTTGCCAGAGGCATTCACTTCTGGCGCCGCCATCGAGGGGGAcTTCAGAGAT
     R  N  P  L  P  E  A  F  T  S  G  A  A  I  E  G  D  F  R  D
 721 CTCTCGGAACATATTAATGAACCGGTTGATGCGATAATTACGAGCCCTCCATTCATGGGA
     L  S  E  H  I  N  E  P  V  D  A  I  I  T  S  P  P  F  M  G
 781 ATGCGTTTCGATCGGCCTAATTGGCTTCGCCTGTGGTTCTGCGGATGGGACGCTGAGGAC
     M  R  F  D  R  P  N  W  L  R  L  W  F  C  G  W  D  A  E  D
 841 TTCTGGACGACAAGCCTGGGTTTTTTGGAGCGCCACCAAGTGAAATCGCGGGATTCCTAC
     F  W  T  T  S  L  G  F  L  E  R  H  Q  V  K  S  R  D  S  Y
 901 ATCGATTTTTTCGAGATGTCCATCAAGACGTTGAAGCAAGACGGCTTGCTTGTCATGCAT
     I  D  F  F  E  M  S  I  K  T  L  K  Q  D  G  L  L  V  M  H
 961 CTGGGGAGTGGCGGGAAAAAGAATCTTGTCAACGATCTCAAGTCCCTCGCGGTACCGCTT
     L  G  S  G  G  K  K  N  L  V  N  D  L  K  S  L  A  V  P  L
1021 TTTGAACTTGCAGGCGAGGTGATCGAAGACGTGGACGACCATCAGACACATGGAATTCGA
     F  E  L  A  G  E  V  I  E  D  V  D  D  H  Q  T  H  G  I  R
1081 GACCGAGGCCTTACAACTAAACATCATCTCCTGTTCTTCAAACCTGCATAG
     D  R  G  L  T  T  K  H  H  L  L  F  F  K  P  A  *
```

FIG. 3

```
   1 ATGAGCGTCGATGCACCTTCGCCTGCTCGCCGCCGGGGTCAAGCTGCTACCTCCGGACGA
     M  S  V  D  A  P  S  P  A  R  R  R  G  Q  A  A  T  S  G  R
  61 GGAACAAATGAAAATAGATTGCCAATTGACCTCGGGGTAACCTTCCGGGACAACAGAAAC
     G  T  N  E  N  R  L  P  I  D  L  G  V  T  F  R  D  N  R  N
 121 CGGCCTGTTCATTCATGGTATCCATATGTAGAGGGGTTCTCGGCCGCTTACGTGGAGGGC
     R  P  V  H  S  W  Y  P  Y  V  E  G  F  S  A  A  Y  V  E  G
 181 GTCTTGGCGCCCTATAATGGGCACAACGTAGCAGTTTATGACCCATTTGGCGGGTCTGGC
     V  L  A  P  Y  N  G  H  N  V  A  V  Y  D  P  F  G  G  S  G
 241 ACACTGCAATCGACAGCGTCGTGGCTCGGTATCAATTCGTTCTATTCAGAAGTCAATCCT
     T  L  Q  S  T  A  S  W  L  G  I  N  S  F  Y  S  E  V  N  P
 301 TTCATGCGCTTTGTGGCCGAAGCCAAGGTTAACGCAACATTGAAGGCTGCGCAGAATAAG
     F  M  R  F  V  A  E  A  K  V  N  A  T  L  K  A  A  Q  N  K
 361 GACGTCTTTCGTTGTGCCGCCAAGGAATTTCTAGACATGCTCAGCGAGAAGGAATTGGCA
     D  V  F  R  C  A  A  K  E  F  L  D  M  L  S  E  K  E  L  A
 421 CACCGAGGACGCTCTGTCGATCTTTCGCAGTATTATAGCGCTTTCCCGGGGCGCGACTTC
     H  R  G  R  S  V  D  L  S  Q  Y  Y  S  A  F  P  G  R  D  F
 481 TTTGAAGAAGAACATATTCGCCAATTGTTGGCTGCTTGCGATGCCGCACGACTTATCGGT
     F  E  E  E  H  I  R  Q  L  L  A  A  C  D  A  A  R  L  I  G
 541 TCTGATTATGCTTGGGTTCGGCAGCTCCTCTTGCTGGCCTGCGCTGCAAATGcCGTACAT
     S  D  Y  A  W  V  R  Q  L  L  L  L  A  C  A  A  N .A  V  H
 601 AGTTCAAACATGACGCGTAGGGCAGACCTCCGTAGGCGGCGCCAAAATGAATACATCAAC
     S  S  N  M  T  R  R  A  D  L  R  R  R  R  Q  N  E  Y  I  N
 661 CGGAAGGTTGATGTGGCGCGATTCATTTCTGATACGGTTCAAGCAATGCTCGACGATGTC
     R  K  V  D  V  A  R  F  I  S  D  T  V  Q  A  M  L  D  D  V
 721 GAGCAGGTCCCCTTTGGAGCGGTAGCATCACATTATGTTTCCGATGACTGCCGAGACCTT
     E  Q  V  P  F  G  A  V  A  S  H  Y  V  S  D  D  C  R  D  L
 781 CCTAGTCGATATATAGATTGTTTCGATATCGCTATCACCTCCCCGCCATACCTCAACGGA
     P  S  R  Y  I  D  C  F  D  I  A  I  T  S  P  P  Y  L  N  G
 841 ACAAACTATTTCAGAAATACGAAGATTGAGCTATGGTTGCTGGGGTTTTTGAGTCACGAG
     T  N  Y  F  R  N  T  K  I  E  L  W  L  L  G  F  L  S  H  E
 901 AGTGAGTTGCCaAAATTTTGCCGAGAGGCTATCACTGCAGGcATTAATAATGTAAGCGGA
     S  E  L  P  K  F  C  R  E  A  I  T  A  G  I  N  N  V  S  G
 961 AATAAGGCGCTCGATCACCATTTCGACGTCGTGGAGGATGTGGCCACGAAGCTGGATGAT
     N  K  A  L  D  H  H  F  D  V  V  E  D  V  A  T  K  L  D  D
1021 GTGGCACCGGATCGGCGAATCCCAAAGCTTGTCCGCCATTATTTTTCCGATATGTACGAA
     V  A  P  D  R  R  I  P  K  L  V  R  H  Y  F  S  D  M  Y  E
1081 GTACTAACGTCAGTGAGAAGTTCTCTTCGTTTGGGAGGAAGGTTCATTCTGGATATCGGC
     V  L  T  S  V  R  S  S  L  R  L  G  G  R  F  I  L  D  I  G
1141 GATTCCAAGTTCTATGGAGTCCATGTCCCCGTCGATCGTATTTTGGTGGAGTTGGGTAAG
     D  S  K  F  Y  G  V  H  V  P  V  D  R  I  L  V  E  L  G  K
1201 CAAGTCGGGTTTCAACTTCATCAAGATGTAGTAATCGCTAGGCGACACTCTCGGGATAAA
     Q  V  G  F  Q  L  H  Q  D  V  V  I  A  R  R  H  S  R  D  K
1261 ACTCCGCTTGTCCAGGTTGAGCTCGAGTTCAGGAAGGCCTAG
     T  P  L  V  Q  V  E  L  E  F  R  K  A  *
```

FIG. 4

```
   1 ATGCGGAGGCTTGCTACACAACGACGCGAGGACGCGTACAAATCAAATAGGGATTATCAG
     M  R  R  L  A  T  Q  R  R  E  D  A  Y  K  S  N  R  D  Y  Q
  61 ACCGTGCACGAAGCTCAGAGCCTTCGAGTCAACTCGACCGATGATGACAACCTGAGCCTC
     T  V  H  E  A  Q  S  L  R  V  N  S  T  D  D  D  N  L  S  L
 121 TTCCTCTTGAAAGATATTTCACCCCGCGAAGATTCTAAAAATATTGTAGGATTTGGAGGC
     F  L  L  K  D  I  S  P  R  E  D  S  K  N  I  V  G  F  G  G
 181 TTCGTCAAGCCCGAAATCGCCACCACCATGGCGCTTACCTTAACGACAGACATCGATAAA
     F  V  K  P  E  I  A  T  T  M  A  L  T  L  T  T  D  I  D  K
 241 CAAATAAAATCAGTGCCGTTATCCTCGAATTGGAATCGGATCAGCATCGTTGCAAAGTTC
     Q  I  K  S  V  P  L  S  S  N  W  N  R  I  S  I  V  A  K  F
 301 GCGAGCAACCCGTCTGTTAGCATTACTCTGGGATTTGATCAAACCCCATGGGTCGATTTC
     A  S  N  P  S  V  S  I  T  L  G  F  D  Q  T  P  W  V  D  F
 361 TGGGGNATCAATTCGGACGATATCGGCCTTTCATTTGTATCGGACGCAGTCCCTCTTGAA
     W  G  I  N  S  D  D  I  G  L  S  F  V  S  D  A  V  P  L  E
 421 ATGAGCATGATTGATAGCATACATATTGCCCCCGAAACACTATACCTTGATCACTCAAGC
     M  S  M  I  D  S  I  H  I  A  P  E  T  L  Y  L  D  H  S  S
 481 GCATGTCTCCTTGACATTGATCCAGTGGAATCGACACGCTTCAAAACAGGRCATGGTGAC
     A  C  L  L  D  I  D  P  V  E  S  T  R  F  K  T  G  H  G  D
 541 CCTTTAAGTCTGAAGAGATGGTCATACTGGGGGCGCCTTCTTCCTATAGACCTCGAGCGT
     P  L  S  L  K  R  W  S  Y  W  G  R  L  L  P  I  D  L  E  R
 601 CCCGGCAAGCTGTCTTTTCACAAACATCGAGCCAAAATCACTAATCATCAGAACGAGTGT
     P  G  K  L  S  F  H  K  H  R  A  K  I  T  N  H  Q  N  E  C
 661 CGTTCATGTAAGAAGTGGCGAATAAACATCTCCTTCAATCCGATGCGCACGATTGACCAG
     R  S  C  K  K  W  R  I  N  I  S  F  N  P  M  R  T  I  D  Q
 721 CTTAACGAGTCAGCACTTATCACACGTGAGCGAAAGATATTCCTGCAAGAACCAGAAATT
     L  N  E  S  A  L  I  T  R  E  R  K  I  F  L  Q  E  P  E  I
 781 CTTCAGGAAATTAAGGATAGGACCGGCGCGGGACTTAAAAGTCAAGTGTGGGAACGATTC
     L  Q  E  I  K  D  R  T  G  A  G  L  K  S  Q  V  W  E  R  F
 841 CATCGCAAGTGCTTCAACTGTAGAAAAGATCTCAAACTAAGCGAGGTTCAACTGGACCAC
     H  R  K  C  F  N  C  R  K  D  L  K  L  S  E  V  Q  L  D  H
 901 ACTCGGCCGCTTGCATACCTATGGCCGATTGATGAGCATGCGACTTGCTTGTGCGCACAA
     T  R  P  L  A  Y  L  W  P  I  D  E  H  A  T  C  L  C  A  Q
 961 TGCAACAATACCAAAAAAGACCGCTTTCCTGTAGATTTCTATAGCGAACAGCAGATACGC
     C  N  N  T  K  K  D  R  F  P  V  D  F  Y  S  E  Q  Q  I  R
1021 GAACTGTCGGACATTTGCGGACTTCCGTATCAGGATCTATGTGCTCGCTCGTTGAATTTA
     E  L  S  D  I  C  G  L  P  Y  Q  D  L  C  A  R  S  L  N  L
1081 GATCAACTCGATAGGATCGAGCGTAATATCGCAGAGTTCTCCAAAGAATGGGATGTAAGA
     D  Q  L  D  R  I  E  R  N  I  A  E  F  S  K  E  W  D  V  R
1141 ACTTTCGCATCAACCGCCCGGAGAATATCGGAAGTTTACCCCGCGCGAGACCTATTTGAA
     T  F  A  S  T  A  R  R  I  S  E  V  Y  P  A  R  D  L  F  E
1201 ACTCTTAAGAAGGAAAGCGAGTCAGCGTACAATAAAATTATTGAGAAGTTGAAGGAAAGA
     T  L  K  K  E  S  E  S  A  Y  N  K  I  I  E  K  L  K  E  R
1261 CCAGACGCACTTCTCGATGAAGCACTACCACTGGACTGA
     P  D  A  L  L  D  E  A  L  P  L  D  *
```

FIG. 5

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 1131 base pairs
( B ) TYPE: nucleic acid
( C ) STRANDEDNESS: single
( D ) TOPOLOGY: linear ( i i ) MOLECULE TYPE: genomic DNA ( i x ) FEATURE:
( A ) NAME/KEY: Coding Sequence
( B ) LOCATION: 1...1128
( D ) OTHER INFORMATION:

( x i ) SEQUENCE DESCRIPTION: SEQ ID NO:1:

```
GTG  TTG  GAA  ACT  CTT  GAG  CTA  GTC  AAC  AAA  ATT  GCG  GAG  TTT  CAA  AGG    48
Met  Leu  Glu  Thr  Leu  Glu  Leu  Val  Asn  Lys  Ile  Ala  Glu  Phe  Gln  Arg
 1             5                   10                  15
```

-continued

| | | | | | | | | | | | | | | |
|---|---|---|---|---|---|---|---|---|---|---|---|---|---|---|
| AAG | CTA | CCT | TAC | ACG | CAG | GAC | GAC | TAT | AAG | AGT | CGC | TCC | TGG | GGG | CAC 96 |
| Lys | Leu | Pro 20 | Tyr | Thr | Gln | Asp | Asp | Tyr 25 | Lys | Ser | Arg | Ser | Trp 30 | Gly | His |

CCC TTG CAC TCC CTT TGT TCG TAC CAG GGA AAG TTG AAA CCT TCG CTT 144
Pro Leu His Ser Leu Cys Ser Tyr Gln Gly Lys Leu Lys Pro Ser Leu
           35                    40                 45

GCT CAC TGG CTC GTT AAG ACA TTC TCG CCG GAA GGT GGC ACG GTA CTC 192
Ala His Trp Leu Val Lys Thr Phe Ser Pro Glu Gly Gly Thr Val Leu
     50                     55                  60

GAT CCG ATG GGA GGC GTG GGA ACA ATA GCC TTT GAA GCG GCT CTA ACG 240
Asp Pro Met Gly Gly Val Gly Thr Ile Ala Phe Glu Ala Ala Leu Thr
65              70                      75                   80

GGT CGG GTC GGG ATA ACC AAC GAC AAA AGT CCA TTG GCC GCT ACT GTC 288
Gly Arg Val Gly Ile Thr Asn Asp Lys Ser Pro Leu Ala Ala Thr Val
             85                  90                       95

ACC GCC GGC AAG CTT GCC CCG TCG TCT ATA CTG GAA GCT GAA GAG GCC 336
Thr Ala Gly Lys Leu Ala Pro Ser Ser Ile Leu Glu Ala Glu Glu Ala
            100                 105                 110

ATT GGT CGA CTG GCG GAA GAT ATT GAA TCG GTG GAC CTC AGT GCT GCA 384
Ile Gly Arg Leu Ala Glu Asp Ile Glu Ser Val Asp Leu Ser Ala Ala
        115                 120                 125

GAT TAT GAA GCC GCC AAT TTC GGC TTG AAT GCA CGC GTT TCT GAC TAC 432
Asp Tyr Glu Ala Ala Asn Phe Gly Leu Asn Ala Arg Val Ser Asp Tyr
130                 135                 140

TAT CAC CCG GAT ACT CTC AAA GAG ATT TTG CGC GCG CGC CGT ATT TTT 480
Tyr His Pro Asp Thr Leu Lys Glu Ile Leu Arg Ala Arg Arg Ile Phe
145                 150                 155                 160

AGC GAG AGA CGA GAA GCT TAC CCA GCA TTT GTC TGG GCA TCT TTG TTG 528
Ser Glu Arg Arg Glu Ala Tyr Pro Ala Phe Val Trp Ala Ser Leu Leu
                165                 170                 175

CAT GTA CTG CAT GGA AAT CGG CCA TAT GCG TTG TCG CGG ATT TCG CAC 576
His Val Leu His Gly Asn Arg Pro Tyr Ala Leu Ser Arg Ile Ser His
            180                 185                 190

CCA ATT ACA CCT TTC AAC CCG TCA GGG GTA GCT GAG TAC AGA TCG GTA 624
Pro Ile Thr Pro Phe Asn Pro Ser Gly Val Ala Glu Tyr Arg Ser Val
        195                 200                 205

GTC GAG AAG ATT GCC CAC CGC GCC CGG CTT GCT CTA AGG AAT CCG TTG 672
Val Glu Lys Ile Ala His Arg Ala Arg Leu Ala Leu Arg Asn Pro Leu
    210                 215                 220

CCA GAG GCA TTC ACT TCT GGC GCC GCC ATC GAG GGG GAC TTC AGA GAT 720
Pro Glu Ala Phe Thr Ser Gly Ala Ala Ile Glu Gly Asp Phe Arg Asp
225                 230                 235                 240

CTC TCG GAA CAT ATT AAT GAA CCG GTT GAT GCG ATA ATT ACG AGC CCT 768
Leu Ser Glu His Ile Asn Glu Pro Val Asp Ala Ile Ile Thr Ser Pro
                245                 250                 255

CCA TTC ATG GGA ATG CGT TTC GAT CGG CCT AAT TGG CTT CGC CTG TGG 816
Pro Phe Met Gly Met Arg Phe Asp Arg Pro Asn Trp Leu Arg Leu Trp
            260                 265                 270

TTC TGC GGA TGG GAC GCT GAG GAC TTC TGG ACG ACA AGC CTG GGT TTT 864
Phe Cys Gly Trp Asp Ala Glu Asp Phe Trp Thr Thr Ser Leu Gly Phe
        275                 280                 285

TTG GAG CGC CAC CAA GTG AAA TCG CGG GAT TCC TAC ATC GAT TTT TTC 912
Leu Glu Arg His Gln Val Lys Ser Arg Asp Ser Tyr Ile Asp Phe Phe
290                 295                 300

GAG ATG TCC ATC AAG ACG TTG AAG CAA GAC GGC TTG CTT GTC ATG CAT 960
Glu Met Ser Ile Lys Thr Leu Lys Gln Asp Gly Leu Leu Val Met His
305                 310                 315                 320

CTG GGG AGT GGC GGG AAA AAG AAT CTT GTC AAC GAT CTC AAG TCC CT 1008
Leu Gly Ser Gly Gly Lys Lys Asn Leu Val Asn Asp Leu Lys Ser Leu
                325                 330                 335

```
GCG GTA CCG CTT TTT GAA CTT GCA GGC GAG GTG ATC GAA GAC GTG GA    1056
Ala Val Pro Leu Phe Glu Leu Ala Gly Glu Val Ile Glu Asp Val Asp
        340             345             350

GAC CAT CAG ACA CAT GGA ATT CGA GAC CGA GGC CTT ACA ACT AAA CA    1104
Asp His Gln Thr His Gly Ile Arg Asp Arg Gly Leu Thr Thr Lys His
        355             360             365

CAT CTC CTG TTC TTC AAA CCT GCA TAG                               1131
His Leu Leu Phe Phe Lys Pro Ala
        370             375
```

( 2 ) INFORMATION FOR SEQ ID NO:2:

( i ) SEQUENCE CHARACTERISTICS:
        ( A ) LENGTH: 1302 base pairs
        ( B ) TYPE: nucleic acid
        ( C ) STRANDEDNESS: single
        ( D ) TOPOLOGY: linear     ( i i ) MOLECULE TYPE: genomic DNA     ( i x ) FEATURE:
        ( A ) NAME/KEY: Coding Sequence
        ( B ) LOCATION: 1...1299

( x i ) SEQUENCE DESCRIPTION: SEQ ID NO:2:

```
ATG AGC GTC GAT GCA CCT TCG CCT GCT CGC CGC CGG GGT CAA GCT GCT    48
Met Ser Val Asp Ala Pro Ser Pro Ala Arg Arg Arg Gly Gln Ala Ala
1               5               10              15

ACC TCC GGA CGA GGA ACA AAT GAA AAT AGA TTG CCA ATT GAC CTC GGG    96
Thr Ser Gly Arg Gly Thr Asn Glu Asn Arg Leu Pro Ile Asp Leu Gly
            20              25              30

GTA ACC TTC CGG GAC AAC AGA AAC CGG CCT GTT CAT TCA TGG TAT CCA   144
Val Thr Phe Arg Asp Asn Arg Asn Arg Pro Val His Ser Trp Tyr Pro
        35              40              45

TAT GTA GAG GGG TTC TCG GCC GCT TAC GTG GAG GGC GTC TTG GCG CCC   192
Tyr Val Glu Gly Phe Ser Ala Ala Tyr Val Glu Gly Val Leu Ala Pro
    50              55              60

TAT AAT GGG CAC AAC GTA GCA GTT TAT GAC CCA TTT GGC GGG TCT GGG   240
Tyr Asn Gly His Asn Val Ala Val Tyr Asp Pro Phe Gly Gly Ser Gly
65              70              75              80

ACA CTG CAA TCG ACA GCG TCG TGG CTC GGT ATC AAT TCG TTC TAT TCA   288
Thr Leu Gln Ser Thr Ala Ser Trp Leu Gly Ile Asn Ser Phe Tyr Ser
            85              90              95

GAA GTC AAT CCT TTC ATG CGC TTT GTG GCC GAA GCC AAG GTT AAC GCA   336
Glu Val Asn Pro Phe Met Arg Phe Val Ala Glu Ala Lys Val Asn Ala
        100             105             110

ACA TTG AAG GCT GCG CAG AAT AAG GAC GTC TTT CGT TGT GCC GCC AAG   384
Thr Leu Lys Ala Ala Gln Asn Lys Asp Val Phe Arg Cys Ala Ala Lys
    115             120             125

GAA TTT CTA GAC ATG CTC AGC GAG AAG GAA TTG GCA CAC CGA GGA CGC   432
Glu Phe Leu Asp Met Leu Ser Glu Lys Glu Leu Ala His Arg Gly Arg
130             135             140

TCT GTC GAT CTT TCG CAG TAT TAT AGC GCT TTC CCG GGG CGC GAC TTC   480
Ser Val Asp Leu Ser Gln Tyr Tyr Ser Ala Phe Pro Gly Arg Asp Phe
145             150             155             160

TTT GAA GAA GAA CAT ATT CGC CAA TTG TTG GCT GCT TGC GAT GCC GCA   528
Phe Glu Glu Glu His Ile Arg Gln Leu Leu Ala Ala Cys Asp Ala Ala
            165             170             175

CGA CTT ATC GGT TCT GAT TAT GCT TGG GTT CGG CAG CTC CTC TTG CTG   576
Arg Leu Ile Gly Ser Asp Tyr Ala Trp Val Arg Gln Leu Leu Leu Leu
        180             185             190

GCC TGC GCT GCA AAT GCC GTA CAT AGT TCA AAC ATG ACG CGT AGG GCA   624
Ala Cys Ala Ala Asn Ala Val His Ser Ser Asn Met Thr Arg Arg Ala
```

```
                                     195                         200                                205
       GAC  CTC  CGT  AGG  CGG  CGC  CAA  AAT  GAA  TAC  ATC  AAC  CGG  AAG  GTT  GAT  672
       Asp  Leu  Arg  Arg  Arg  Arg  Gln  Asn  Glu  Tyr  Ile  Asn  Arg  Lys  Val  Asp
            210                      215                      220

GTG  GCG  CGA  TTC  ATT  TCT  GAT  ACG  GTT  CAA  GCA  ATG  CTC  GAC  GAT  GTC  720
       Val  Ala  Arg  Phe  Ile  Ser  Asp  Thr  Val  Gln  Ala  Met  Leu  Asp  Asp  Val
       225                      230                      235                           240

GAG  CAG  GTC  CCC  TTT  GGA  GCG  GTA  GCA  TCA  CAT  TAT  GTT  TCC  GAT  GAC  768
       Glu  Gln  Val  Pro  Phe  Gly  Ala  Val  Ala  Ser  His  Tyr  Val  Ser  Asp  Asp
                           245                      250                           255

TGC  CGA  GAC  CTT  CCT  AGT  CGA  TAT  ATA  GAT  TGT  TTC  GAT  ATC  GCT  ATC  816
       Cys  Arg  Asp  Leu  Pro  Ser  Arg  Tyr  Ile  Asp  Cys  Phe  Asp  Ile  Ala  Ile
                      260                      265                           270

ACC  TCC  CCG  CCA  TAC  CTC  AAC  GGA  ACA  AAT  TAT  TTC  AGA  AAT  ACG  AAG  864
       Thr  Ser  Pro  Pro  Tyr  Leu  Asn  Gly  Thr  Asn  Tyr  Phe  Arg  Asn  Thr  Lys
                 275                      280                           285

ATT  GAG  CTA  TGG  TTG  CTG  GGG  TTT  TTG  AGT  CAC  GAG  AGT  GAG  TTG  CCA  912
       Ile  Glu  Leu  Trp  Leu  Leu  Gly  Phe  Leu  Ser  His  Glu  Ser  Glu  Leu  Pro
            290                      295                      300

AAA  TTT  TGC  CGA  GAG  GCT  ATC  ACT  GCA  GGC  ATT  AAT  AAT  GTA  AGC  GGA  960
       Lys  Phe  Cys  Arg  Glu  Ala  Ile  Thr  Ala  Gly  Ile  Asn  Asn  Val  Ser  Gly
       305                      310                      315                           320

AAT  AAG  GCG  CTC  GAT  CAC  CAT  TTC  GAC  GTC  GTG  GAG  GAT  GTG  GCC  AC  1008
       Asn  Lys  Ala  Leu  Asp  His  His  Phe  Asp  Val  Val  Glu  Asp  Val  Ala  Thr
                           325                      330                           335

AAG  CTG  GAT  GAT  GTG  GCA  CCG  GAT  CGG  CGA  ATC  CCA  AAG  CTT  GTC  CG  1056
       Lys  Leu  Asp  Asp  Val  Ala  Pro  Asp  Arg  Arg  Ile  Pro  Lys  Leu  Val  Arg
                      340                      345                           350

CAT  TAT  TTT  TCC  GAT  ATG  TAC  GAA  GTA  CTA  ACG  TCA  GTG  AGA  AGT  TC  1104
       His  Tyr  Phe  Ser  Asp  Met  Tyr  Glu  Val  Leu  Thr  Ser  Val  Arg  Ser  Ser
                 355                      360                           365

CTT  CGT  TTG  GGA  GGA  AGG  TTC  ATT  CTG  GAT  ATC  GGC  GAT  TCC  AAG  TT  1152
       Leu  Arg  Leu  Gly  Gly  Arg  Phe  Ile  Leu  Asp  Ile  Gly  Asp  Ser  Lys  Phe
            370                      375                      380

TAT  GGA  GTC  CAT  GTC  CCC  GTC  GAT  CGT  ATT  TTG  GTG  GAG  TTG  GGT  AA  1200
       Tyr  Gly  Val  His  Val  Pro  Val  Asp  Arg  Ile  Leu  Val  Glu  Leu  Gly  Lys
       385                      390                      395                           400

CAA  GTC  GGG  TTT  CAA  CTT  CAT  CAA  GAT  GTA  GTA  ATC  GCT  AGG  CGA  CA  1248
       Gln  Val  Gly  Phe  Gln  Leu  His  Gln  Asp  Val  Val  Ile  Ala  Arg  Arg  His
                           405                      410                           415

TCT  CGG  GAT  AAA  ACT  CCG  CTT  GTC  CAG  GTT  GAG  CTC  GAG  TTC  AGG  AA  1296
       Ser  Arg  Asp  Lys  Thr  Pro  Leu  Val  Gln  Val  Glu  Leu  Glu  Phe  Arg  Lys
                      420                      425                           430

GCC  TAG                                                                         1302
       Ala
```

( 2 ) INFORMATION FOR SEQ ID NO:3:

( i ) SEQUENCE CHARACTERISTICS:
        ( A ) LENGTH: 1299 base pairs
        ( B ) TYPE: nucleic acid
        ( C ) STRANDEDNESS: single
        ( D ) TOPOLOGY: linear     ( i i ) MOLECULE TYPE: genomic DNA     ( i x ) FEATURE:
        ( A ) NAME/KEY: Coding Sequence
        ( B ) LOCATION: 1...1296

( x i ) SEQUENCE DESCRIPTION: SEQ ID NO:3:

```
       ATG  CGG  AGG  CTT  GCT  ACA  CAA  CGA  CGC  GAG  GAC  GCG  TAC  AAA  TCA  AAT   48
       Met  Arg  Arg  Leu  Ala  Thr  Gln  Arg  Arg  Glu  Asp  Ala  Tyr  Lys  Ser  Asn
```

|   | 1 |   |   |   | 5 |   |   |   |   | 10 |   |   |   |   | 15 |   |   |
|---|---|---|---|---|---|---|---|---|---|---|---|---|---|---|---|---|---|
| AGG | GAT | TAT | CAG | ACC | GTG | CAC | GAA | GCT | CAG | AGC | CTT | CGA | GTC | AAC | TCG | 96 |
| Arg | Asp | Tyr | Gln | Thr | Val | His | Glu | Ala | Gln | Ser | Leu | Arg | Val | Asn | Ser |  |
|  |  |  | 20 |  |  |  |  | 25 |  |  |  |  | 30 |  |  |  |
| ACC | GAT | GAT | GAC | AAC | CTG | AGC | CTC | TTC | CTC | TTG | AAA | GAT | ATT | TCA | CCC | 144 |
| Thr | Asp | Asp | Asp | Asn | Leu | Ser | Leu | Phe | Leu | Leu | Lys | Asp | Ile | Ser | Pro |  |
|  |  | 35 |  |  |  |  | 40 |  |  |  |  | 45 |  |  |  |  |
| CGC | GAA | GAT | TCT | AAA | AAT | ATT | GTA | GGA | TTT | GGA | GGC | TTC | GTC | AAG | CCC | 192 |
| Arg | Glu | Asp | Ser | Lys | Asn | Ile | Val | Gly | Phe | Gly | Gly | Phe | Val | Lys | Pro |  |
|  | 50 |  |  |  |  | 55 |  |  |  |  | 60 |  |  |  |  |  |
| GAA | ATC | GCC | ACC | ACC | ATG | GCG | CTT | ACC | TTA | ACG | ACA | GAC | ATC | GAT | AAA | 240 |
| Glu | Ile | Ala | Thr | Thr | Met | Ala | Leu | Thr | Leu | Thr | Thr | Asp | Ile | Asp | Lys |  |
| 65 |  |  |  |  | 70 |  |  |  |  | 75 |  |  |  |  | 80 |  |
| CAA | ATA | AAA | TCA | GTG | CCG | TTA | TCC | TCG | AAT | TGG | AAT | CGG | ATC | AGC | ATC | 288 |
| Gln | Ile | Lys | Ser | Val | Pro | Leu | Ser | Ser | Asn | Trp | Asn | Arg | Ile | Ser | Ile |  |
|  |  |  |  | 85 |  |  |  |  | 90 |  |  |  |  | 95 |  |  |
| GTT | GCA | AAG | TTC | GCG | AGC | AAC | CCG | TCT | GTT | AGC | ATT | ACT | CTG | GGA | TTT | 336 |
| Val | Ala | Lys | Phe | Ala | Ser | Asn | Pro | Ser | Val | Ser | Ile | Thr | Leu | Gly | Phe |  |
|  |  |  | 100 |  |  |  |  | 105 |  |  |  |  | 110 |  |  |  |
| GAT | CAA | ACC | CCA | TGG | GTC | GAT | TTC | TGG | GGN | ATC | AAT | TCG | GAC | GAT | ATC | 384 |
| Asp | Gln | Thr | Pro | Trp | Val | Asp | Phe | Trp | Xaa | Ile | Asn | Ser | Asp | Asp | Ile |  |
|  |  | 115 |  |  |  |  | 120 |  |  |  |  | 125 |  |  |  |  |
| GGC | CTT | TCA | TTT | GTA | TCG | GAC | GCA | GTC | CCT | CTT | GAA | ATG | AGC | ATG | ATT | 432 |
| Gly | Leu | Ser | Phe | Val | Ser | Asp | Ala | Val | Pro | Leu | Glu | Met | Ser | Met | Ile |  |
|  | 130 |  |  |  |  | 135 |  |  |  |  | 140 |  |  |  |  |  |
| GAT | AGC | ATA | CAT | ATT | GCC | CCC | GAA | ACA | CTA | TAC | CTT | GAT | CAC | TCA | AGC | 480 |
| Asp | Ser | Ile | His | Ile | Ala | Pro | Glu | Thr | Leu | Tyr | Leu | Asp | His | Ser | Ser |  |
| 145 |  |  |  |  | 150 |  |  |  |  | 155 |  |  |  |  | 160 |  |
| GCA | TGT | CTC | CTT | GAC | ATT | GAT | CCA | GTG | GAA | TCG | ACA | CGC | TTC | AAA | ACA | 528 |
| Ala | Cys | Leu | Leu | Asp | Ile | Asp | Pro | Val | Glu | Ser | Thr | Arg | Phe | Lys | Thr |  |
|  |  |  |  | 165 |  |  |  |  | 170 |  |  |  |  | 175 |  |  |
| GGR | CAT | GGT | GAC | CCT | TTA | AGT | CTG | AAG | AGA | TGG | TCA | TAC | TGG | GGG | CGC | 576 |
| Xaa | His | Gly | Asp | Pro | Leu | Ser | Leu | Lys | Arg | Trp | Ser | Tyr | Trp | Gly | Arg |  |
|  |  |  | 180 |  |  |  |  | 185 |  |  |  |  | 190 |  |  |  |
| CTT | CTT | CCT | ATA | GAC | CTC | GAG | CGT | CCC | GGC | AAG | CTG | TCT | TTT | CAC | AAA | 624 |
| Leu | Leu | Pro | Ile | Asp | Leu | Glu | Arg | Pro | Gly | Lys | Leu | Ser | Phe | His | Lys |  |
|  |  | 195 |  |  |  |  | 200 |  |  |  |  | 205 |  |  |  |  |
| CAT | CGA | GCC | AAA | ATC | ACT | AAT | CAT | CAG | AAC | GAG | TGT | CGT | TCA | TGT | AAG | 672 |
| His | Arg | Ala | Lys | Ile | Thr | Asn | His | Gln | Asn | Glu | Cys | Arg | Ser | Cys | Lys |  |
|  | 210 |  |  |  |  | 215 |  |  |  |  | 220 |  |  |  |  |  |
| AAG | TGG | CGA | ATA | AAC | ATC | TCC | TTC | AAT | CCG | ATG | CGC | ACG | ATT | GAC | CAG | 720 |
| Lys | Trp | Arg | Ile | Asn | Ile | Ser | Phe | Asn | Pro | Met | Arg | Thr | Ile | Asp | Gln |  |
| 225 |  |  |  |  | 230 |  |  |  |  | 235 |  |  |  |  | 240 |  |
| CTT | AAC | GAG | TCA | GCA | CTT | ATC | ACA | CGT | GAG | CGA | AAG | ATA | TTC | CTG | CAA | 768 |
| Leu | Asn | Glu | Ser | Ala | Leu | Ile | Thr | Arg | Glu | Arg | Lys | Ile | Phe | Leu | Gln |  |
|  |  |  |  | 245 |  |  |  |  | 250 |  |  |  |  | 255 |  |  |
| GAA | CCA | GAA | ATT | CTT | CAG | GAA | ATT | AAG | GAT | AGG | ACC | GGC | GCG | GGA | CTT | 816 |
| Glu | Pro | Glu | Ile | Leu | Gln | Glu | Ile | Lys | Asp | Arg | Thr | Gly | Ala | Gly | Leu |  |
|  |  |  | 260 |  |  |  |  | 265 |  |  |  |  | 270 |  |  |  |
| AAA | AGT | CAA | GTG | TGG | GAA | CGA | TTC | CAT | CGC | AAG | TGC | TTC | AAC | TGT | AGA | 864 |
| Lys | Ser | Gln | Val | Trp | Glu | Arg | Phe | His | Arg | Lys | Cys | Phe | Asn | Cys | Arg |  |
|  |  | 275 |  |  |  |  | 280 |  |  |  |  | 285 |  |  |  |  |
| AAA | GAT | CTC | AAA | CTA | AGC | GAG | GTT | CAA | CTG | GAC | CAC | ACT | CGG | CCG | CTT | 912 |
| Lys | Asp | Leu | Lys | Leu | Ser | Glu | Val | Gln | Leu | Asp | His | Thr | Arg | Pro | Leu |  |
|  | 290 |  |  |  |  | 295 |  |  |  |  | 300 |  |  |  |  |  |
| GCA | TAC | CTA | TGG | CCG | ATT | GAT | GAG | CAT | GCG | ACT | TGC | TTG | TGC | GCA | CAA | 960 |
| Ala | Tyr | Leu | Trp | Pro | Ile | Asp | Glu | His | Ala | Thr | Cys | Leu | Cys | Ala | Gln |  |
| 305 |  |  |  |  | 310 |  |  |  |  | 315 |  |  |  |  | 320 |  |
| TGC | AAC | AAT | ACC | AAA | AAA | GAC | CGC | TTT | CCT | GTA | GAT | TTC | TAT | AGC | GA | 1008 |
| Cys | Asn | Asn | Thr | Lys | Lys | Asp | Arg | Phe | Pro | Val | Asp | Phe | Tyr | Ser | Glu |  |

```
                          325                      330                         335
     CAG  CAG  ATA  CGC  GAA  CTG  TCG  GAC  ATT  TGC  GGA  CTT  CCG  TAT  CAG  GA 1056
     Gln  Gln  Ile  Arg  Glu  Leu  Ser  Asp  Ile  Cys  Gly  Leu  Pro  Tyr  Gln  Asp
               340                      345                      350

CTA  TGT  GCT  CGC  TCG  TTG  AAT  TTA  GAT  CAA  CTC  GAT  AGG  ATC  GAG  CG 1104
     Leu  Cys  Ala  Arg  Ser  Leu  Asn  Leu  Asp  Gln  Leu  Asp  Arg  Ile  Glu  Arg
               355                      360                      365

AAT  ATC  GCA  GAG  TTC  TCC  AAA  GAA  TGG  GAT  GTA  AGA  ACT  TTC  GCA  TC 1152
     Asn  Ile  Ala  Glu  Phe  Ser  Lys  Glu  Trp  Asp  Val  Arg  Thr  Phe  Ala  Ser
               370                      375                      380

ACC  GCC  CGG  AGA  ATA  TCG  GAA  GTT  TAC  CCC  GCG  CGA  GAC  CTA  TTT  GA 1200
     Thr  Ala  Arg  Arg  Ile  Ser  Glu  Val  Tyr  Pro  Ala  Arg  Asp  Leu  Phe  Glu
     385                      390                      395                      400

ACT  CTT  AAG  AAG  GAA  AGC  GAG  TCA  GCG  TAC  AAT  AAA  ATT  ATT  GAG  AA 1248
     Thr  Leu  Lys  Lys  Glu  Ser  Glu  Ser  Ala  Tyr  Asn  Lys  Ile  Ile  Glu  Lys
                         405                      410                      415

TTG  AAG  GAA  AGA  CCA  GAC  GCA  CTT  CTC  GAT  GAA  GCA  CTA  CCA  CTG  GA 1298
     Leu  Lys  Glu  Arg  Pro  Asp  Ala  Leu  Leu  Asp  Glu  Ala  Leu  Pro  Leu  Asp
                         420                      425                      430

A                                                                            1299
```

(2) INFORMATION FOR SEQ ID NO:4:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:4:

```
     Val  Xaa  Asp  Pro  Xaa  Gly  Gly  Xaa  Gly  Thr
     1               5                        10
```

(2) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear     ( i i ) MOLECULE TYPE: single-stranded DNA     ( x i ) SEQUENCE DESCRIPTION: SEQ ID NO:5:

```
     TAAGCTATCT  TGGTCAGTCA  AAG                                          23
```

(2) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: single-stranded DNA     ( x i ) SEQUENCE DESCRIPTION: SEQ ID NO:6:

```
     AACAGGAGAT  GATGTTTAGT  TGTA                                         24
```

(2) INFORMATION FOR SEQ ID NO:7:

( i ) SEQUENCE CHARACTERISTICS:
        ( A ) LENGTH: 27 base pairs
        ( B ) TYPE: nucleic acid (C) STRANDEDNESS: unknown
(D) TOPOLOGY: unknown (ii) MOLECULE TYPE: single-stranded DNA (xi) SEQUENCE DESCRIPTION: SEQ ID NO:7:

ATGCGGAGGC TTGCTACACA ACGACGC  27

(2) INFORMATION FOR SEQ ID NO:8:

(i) SEQUENCE CHARACTERISTICS:
    (A) LENGTH: 27 base pairs
    (B) TYPE: nucleic acid
    (C) STRANDEDNESS: unknown
    (D) TOPOLOGY: unknown (ii) MOLECULE TYPE: single-stranded DNA (xi) SEQUENCE DESCRIPTION: SEQ ID NO:8:

TCAGTCCAGT GGTAGTGCTT CATCGAG  27

METHOD FOR CLONING AND PRODUCING THE SAPI RESTRICTION ENDONUCLEASE IN *E. COLI*

BACKGROUND OF THE INVENTION

The present invention relates to recombinant DNA which encodes the SapI restriction endonuclease and modification methylase, as well as the production of SapI restriction endonuclease from the recombinant DNA.

Type II restriction endonucleases are a class of enzymes that occur naturally in bacteria. When they are purified away from other bacterial components, restriction endonucleases can be used in the laboratory to cleave DNA molecules into precise fragments for molecular cloning and gene characterization.

Restriction endonucleases act by recognizing and binding to particular sequences of nucleotides (the 'recognition sequence') along the DNA molecule. Once bound, they cleave the molecule within, or to one side of, the recognition sequence. Different restriction endonucleases have affinity for different recognition sequences. Over two hundred restriction endonucleases with unique specificities have been identified among the many hundreds of bacterial species that have been examined to date.

Bacteria tend to possess at most, only a small number of restriction endonucleases per species. The endonucleases typically are named according to the bacteria from which they are derived. Thus, the species *Deinococcus radiophilus* for example, synthesizes three different restriction endonucleases, named DraI, DraII and DraIII. These enzymes recognize and cleave the sequences 5'TTTAAA3', 5'PuGGNCCPy3' and 5'CACNNNGTG3' respectively. *Escherichia coli* RY13, on the other hand, synthesizes only one enzyme, EcoRI, which recognizes the sequence 5'GAATTC3'.

It is thought that in nature, restriction endonucleases play a protective role in the welfare of the bacterial cell. They enable bacteria to resist infection by foreign DNA molecules like viruses and plasmids that would otherwise destroy or parasitize them. They impart resistance by cleaving invading foreign DNA molecule each time that the recognition sequence occurs. The cleavage that takes place disables many of the infecting genes and renders the DNA susceptible to further degradation by non-specific nucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same recognition sequence as the corresponding restriction endonuclease, but instead of cleaving the DNA, they chemically modify one or other of the nucleotides within the sequence by the addition of a methyl group. Following methylation, the recognition sequence is no longer cleaved by the restriction endonuclease. The DNA of a bacterial cell is always fully modified by virtue of the activity of its modification methylase. It is therefore completely insensitive to the presence of the endogenous restriction endonuclease. It is only unmodified, and therefore identifiably foreign DNA, that is sensitive to restriction endonuclease recognition and cleavage.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

Type II restriction-modification systems are being cloned with increasing frequency. The first cloned systems used bacteriophage infection as a means of identifying or selecting restriction endonuclease clones (EcoRII: Kosykh et al., *Molec. Gen. Genet.* 178:717–719, (1980); HhaII: Mann et al., *Gene* 3:97–112, (1978); PstI: Walder et al., *Proc. Nat. Acad. Sci.* 78:1503–1507, (1981)). Since the presence of restriction-modification systems in bacteria enable them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucl. Acid. Res.* 12:3659–3676, (1984); PaeR7: Gingeras and Brooks, *Proc. Natl. Acad. Sci. USA* 80:402–406, (1983); Theriault and Roy, *Gene* 19:355–359 (1982); PvuII: Blumenthal et al., *J. Bacteriol.* 164:501–509, (1985)).

A third approach, and one that is being used to clone a growing number of systems are now being cloned by selection for an active methylase gene (U.S. Pat. No. 5,200,333 issued Apr. 6, 1993 and BsuRI: Kiss et al., *Nucl. Acid. Res.* 13:6403–6421, (1985)). Since restriction and modification genes are often closely linked, both genes can often be cloned simultaneously. This selection does not always yield a complete restriction system however, but instead yields only the methylase gene (BspRI: Szomolanyi et al., *Gene* 10:219–225, (1980); Bcn I: Janulaitis et al., *Gene* 20:197–204 (1982); Bsu RI: Kiss and Baldauf, *Gene* 21:111–119, (1983); and Msp I: Walder et al., *J. Biol. Chem.* 258:1235–1241, (1983)).

A more recent method (the "endo-blue method") has been described for direct cloning of restriction endonuclease genes in *E. coli* based on the indicator strain of *E. coli* containing the dinD::lacZ fusion (Fomenkov et al., *Nucl. Acids Res.* 22:2399–2403, 1994). This method utilizes the *E. coli* SOS response following DNA damages caused by restriction endonucleases or non-specific nucleases. A number of thermostable nuclease genes (Tth111I, BsoBI, Tf nuclease) have been cloned by this method (U.S. Pat. No. 5,498,535, issued on Mar. 12, 1996).

Another obstacle to cloning these systems in *E. coli* was discovered in the process of cloning diverse methylase genes. Many *E. coli* strains (including those normally used in cloning) have systems that resist the introduction of DNA containing cytostne methylation. (Raleigh and Wilson, *Proc. Natl. Acad. Sci., USA* 83:9070–9074, (1986)). Therefore, it is also necessary to carefully consider which *E. coli* strain(s) to use for cloning.

Because purified restriction endonucleases, and to a lesser extent, modification methylases, are useful tools for characterizing genes in the laboratory, there is a commercial incentive to obtain bacterial strains through recombinant DNA techniques that synthesize these enzymes in abundance. Such strains would be useful because they would simplify the task of purification as well as providing the means for production in commercially useful amounts.

In addition to the above noted problems associated with cloning restriction-modification genes, when such foreign restriction modification systems are cloned and introduced into *E. coli*, sometimes the methylase and endonuclease yield is very low compared to the native endonuclease-producing strain, probably due to inefficient transcription or translation of the genes in *E. coli*. This is particularly true for cloning of Actinomycetes genes into *E. coli* because of the different GC contents of the two microorganisms. It would therefore also be desirable to have a cloning system that allows Actinomycetes genes such as the SapI restriction endonuclease gene from Saccharopolyspora species to be sufficiently expressed in *E. coli* and selected for based on efficient gene expression.

SUMMARY OF THE INVENTION

Figure 1:
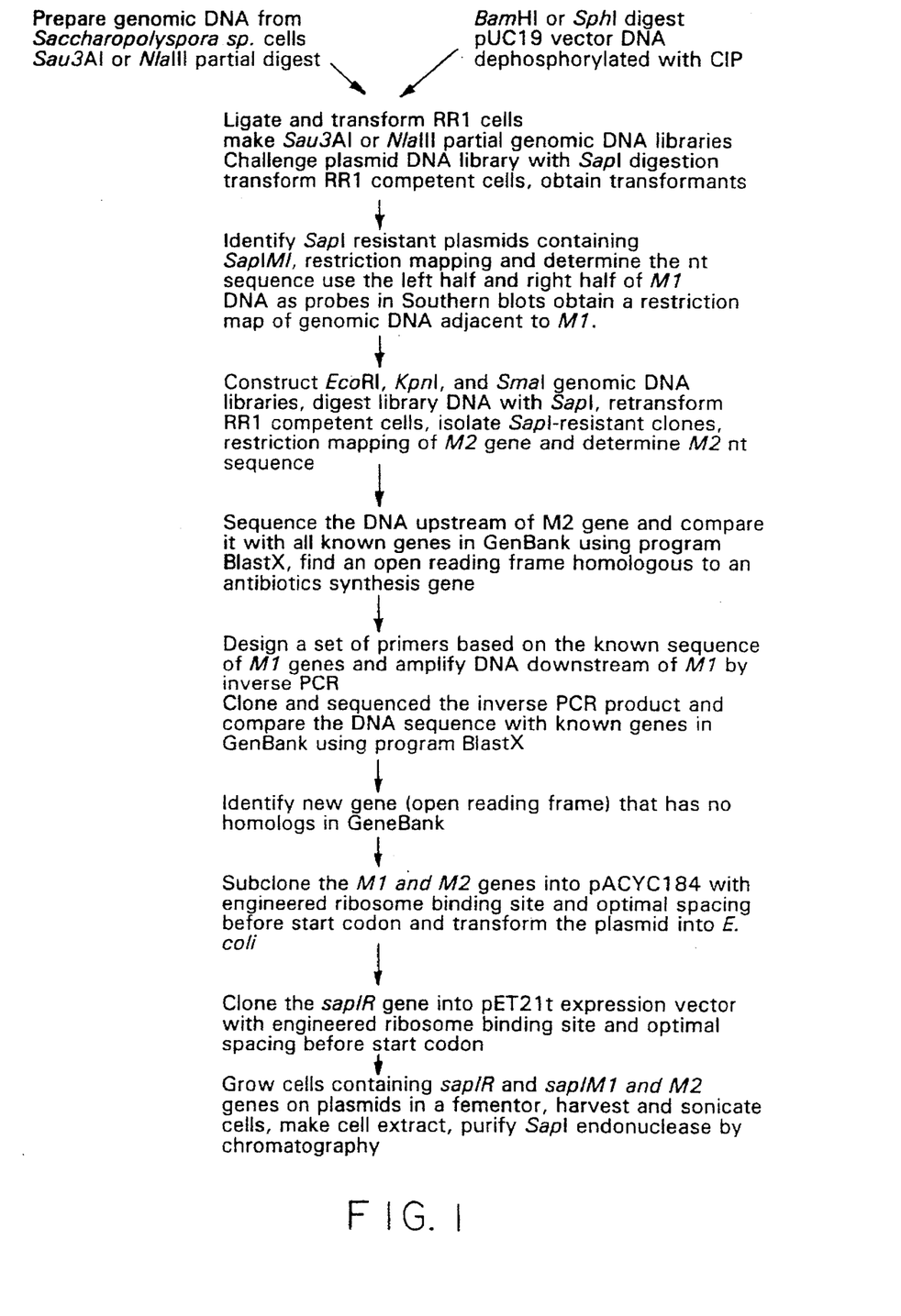
FIG. 1 is a scheme for cloning and producing the SapI restriction endonuclease.

The present invention relates to a method for cloning the SapI restriction-modification system methylase into *E. coli* by a modified methylase selection method. The preferred steps of which are depicted in FIG. 1. In the cloning of the Actinomycete SapI methylase gene, standard methylase gene selection method was used to clone the targeted methylases gene from Saccharopolyspora species, the SapI methylase gene using pUC19 vector. One SapI methylase gene (M1) was cloned. Because the recognition sequence of SapI is asymmetric (5'GCTCTTC3' on one strand and 5'GAAGAGC3' on the opposite strand), it was thought that SapI restriction-modification system might contain two methylases and one endonuclease. A genomic DNA map was obtained using the left half and right half of MI DNA as probes in Southern blots. EcoRI, KpnI, and SmaI genomic DNA libraries were constructed to clone the second methylase gene by the methylase selection method.

After the second SapI methylase gene (M2) was cloned and sequenced, efforts were made to clone and sequence DNA fragments upstream and downstream of the two SapI methylase genes. Usally methylase gene and endonuclease gene in a particular restriction-modification system are located in close proximity to each other. A total of 1731 bp of DNA upstream of M2 gene was sequenced and compared with all known genes in GenBank. It contains a putative gene that has homology to a gene involved in antibiotics synthesis. It was concluded that the SapI restriction endonuclease is not located upstream of M2, but instead may be located downstream of M1 gene. NlaIII partial genomic library was constructed to clone larger genomic inserts that carry M1 and downstream DNA. The downstream DNA was screened from the NlaIII library and sequenced. It only extended further out 657 bp, not large enough to encode the entire endonuclease gene. Inverse PCR was then used to amplify and clone the rest of what was believed to comprise the endonuclease gene.

Figure 2:
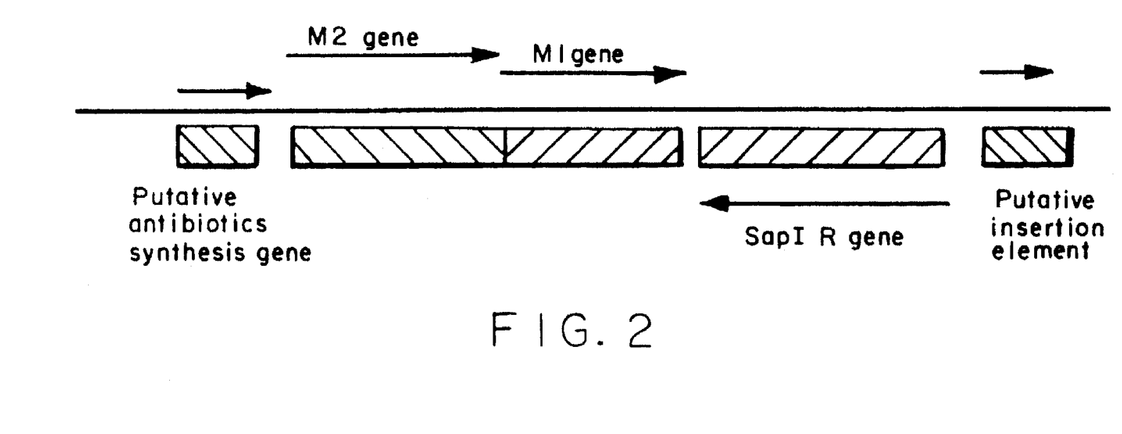
FIG. 2 is a diagram of gene organizations of SapI restriction-modification sytem.

After two separate inverse PCR amplifications, DNA fragments downstream of M1 were cloned and sequenced and one open reading frame was discovered. This ORF does not share any homology to the known genes in the GenBank and was presumed to be the SapI restriction endonuclease gene. The gene organization of SapI restriction-modification system is shown in FIG. 2. The M1 and M2 genes were cloned into pACYC184 or pSC101-derived vectors and transformed into *E. coli* to premodify chromosomal DNA.

The putative SapI endonuclease gene was amplified by PCR and cloned into pUC19 and transformed into the premodified *E. coli* host. Plasmids carrying inserts in pUC19 displayed low SapI endonuclease activity in cell extracts, but all isolates lost activity in large cultures, indicating the clones were not stable. To stabalize the expression clone, efficient ribosome binding site was incorporated in front of M2 and cloned into pACYC184. The M1 gene was also cloned into the same vector. The SapI endonuclease gene was cloned into a T7 expression vector (pET21 derivative) that carried transcription terminators upstream of the T7 promotor. The transcription terminators further reduced the basal level of gene expression under uninduced condition. The endonuclease gene was amplified by PCR and inserted into the T7 expression vector. The final construct was more stable than pUC19-SapIR.

BRIEF DESCRIPTION OF THE DRAWINGS

FIG. 3 is the DNA sequence (SEQ ID NO:1) of sapIM1 gene and its encoded protein sequence.

FIG. 4 is the DNA sequence (SEQ ID NO:2) of sapIM2 gene and its encoded protein sequence.

FIG. 5 is the DNA sequence (SEQ ID NO:3) of sapIR gene and its encoded protein sequence.

FIG. 6 shows the construction of pR976. Vector pR976 is a pACYC184 derivative that carries a $P_{tac}$ promoter and multiple cloning sites downstream of the $P_{tac}$ promoter. It also carries lacI gene that encodes the Lac repressor to regulate gene expression from the $P_{tac}$ promoter (Amann, et al., *Gene* 25:167–178 (1983)).

DETAILED DESCRIPTION OF THE INVENTION

The method described herein by which the SapI methylase genes and endonuclease gene are cloned and expressed is illustrated in FIG. 1 and includes the following steps: 1. The genomic DNA of Saccharopolyspora species was purified.

2. The DNA is digested partially with a restriction endonuclease such as Sau3AI or NlaIII, or any of its isoschizomers, that generates a DNA fragment(s) containing the entire SapI methylase gene. The DNA fragments ranging between 2–20 kb were gel-purified.

3. The Sau3AI-digested genomic DNA of step 2 was ligated into BamHI-cleaved/CIP treated pUC19 cloning vector. The NlaIII-digested genomic DNA was ligated into SphI-cleaved/CIP treated pUC19 cloning vector. The resulting mixtures were used to transform an appropriate host, i.e. a HsdR⁻, McrBC⁻, Mrr⁻ strain, such as *E. coli* strain RR1. The DNA/cell mixtures were plated on ampicillin selective media for transformed cells. After incubation, the transformed colonies were harvested together to form the primary cell library.

4. The recombinant plasmids were purified in toto from the primary cell library to make primary plasmid library. The purified plasmid library was then digested to completion in vitro with SapI endonuclease, or any SapI isoschizomer. SapI endonuclease digestion causes the selective destruction of unmodified, non-methylase-containing clones, resulting in an increase in the relative frequency of SapI methylase-carrying clones.

5. Identification of SapI methylase clone: The digested plasmid library DNA was transformed back into a host such as *E. coli* strain RR1 and transformed colonies were again obtained by plating on ampicillin plates. The colonies were picked and their plasmid DNAs were prepared and analyzed for the presence of the SapI methylase gene by incubating purified plasmid DNA in vitro with SapI endonuclease to determine whether it is resistant to SapI digestion.

6. Once it has been established that the methylase gene has been closed, the clone was analyzed by restriction mapping and deletion mapping. The entire insert was sequenced and one open reading frame corresponding the SapI M1 methylase gene was found. (See FIG. 3, SEQ ID NO:1).

7. To construct a genomic DNA map adjacent to the M1 gene, two DNA fragments from the M1 clone (ClaI-SmaI fragment and Clai-SphI fragment) were used as probes in Southern blots to detect genomic DNA that had been digested by AatII, EcoO109I, EcoRI, KpnI, PvuI, SmaI, SphI, SspI, XbaI, XmnI, AflII, AvrII, BsgI, BspEI, BstBi, Bsu36I, DraIII, EagI, Eco47III, EcoNI, MscI, SnaBI, SpeI, or StyI. The Southern blots indicated that EcoRI (11 kb), KpnI (5.8 kb), and SmaI (6.5 kb) fragments were good candidates for clonging of SapI M2 gene and/or SapI restriction endonuclease gene.

8. The genomic DNA was digested with EcoRI, KpnI, or SmaI. EcoRI fragments around 11 kb, KpnI fragments about 5.8 kb, and SmaI fragments about 6.5 kb were gel-purified and ligated into EcoRI, KpnI, or SmaI digested and CIP treated pUC19 vectors and the ligated DNAs were transformed into RR1 competent cells to construct EcoRI, KpnI, and SmaI genomic DNA libraries. The library DNAs were mixed together and digested with SapI restriction endonuclease and retransformed into RR1 competent cells to screen SapI resistant clones.

9. Three clones with 5.8 kb KpnI fragment insert were isolated that showed partial resistance to SapI digestion. They were analysed by restriction mapping and deletion mapping. Subclones were sequenced. An open reading frame was found to code for a second methylase (M2). (See FIG. 4, SEQ ID NO:2)

10. The 5.8 kb KpnI fragment insert contains the entire M2 gene and majority of M1 gene. The DNA upstream of M2 was sequenced in the hope of locating an open reading frame. A total of 1731 bp of DNA was sequenced upstream of M2 gene and this new sequence was compared with all known genes in GenBank. An open reading frame was found that has homology to the abaA gene involved in antibiotics synthesis. It was concluded that SapI restriction endonuclease gene is not located upstream of M2 gene.

11. Inverse PCR was used to amplify DNA sequences that are downstream of M1 gene. Saccharopolyspora sp. genomic DNA was digested with AflIII, AgeI, AseI, BglII, BsaHI, BsrFI, BstYI, ClaI, EcoRI, KasI, KpnI, MluI, NgoMI, PaeR7I, Ppu10I, or PstI restriction enzymes or any other restriction enzymes that will give rise to reasonable size template DNA (less than 10 kb) for inverse PCR reaction. The digested DNA were self-ligated at a low DNA concentration (less than 2 microgram per ml). The ligated circular DNA was used as templates for inverse PCR reaction using a set of primers (see Example I, Section 5) that annealed to the end of the SapI M1 gene.

12. Amplified products were found in AflIII, AgeI, AseI, BsaHI, BsrFI, BstYI, ClaI, KasI, MluI, PaeR7I, and Ppu10I digested and self-ligated DNA templates used in inverse PCR. The inverse PCR products from ClaI (1.4 kb) and NsiI (1.6 kb) reactions were treated with T4 polynucleotide kinase and T4 DNA polymerase and cloned into HincII-cleaved/CIP treated pUC19 vector. The entire inserts were sequenced. One open reading frame which encoded the SapI endonuclease gene (FIG. 5, SEQ ID NO:3) was found that runs in the opposite direction as compared to M1 gene.

13. The SapI M1 and M2 genes were cloned into pACYC184 to premodify E. coli host. The entire open reading frame (SapI endonuclease gene) was amplified by PCR with two primers. An efficient ribosome binding site and 7 bp spacing were engineered before the ATG start codon. The endonuclease gene was first cloned into high-copy-number expression vectors such as pUC19. But the clones were not stable. SapI endonuclease activity can be found from cell extract of 10 ml culture, but not from 500 ml culture. To stabilize the clone, the endonuclease gene was inserted into a modified T7 expression vector pET21t and transformed into SapI methylase modified cells. ER2504 [pACYC-SapIM1-M2, pET21t-SapIR] (NEB#998; New England Biolabs, Inc.; Beverly, Mass.) produced about 20,000 units of SapI endonuclease activity per gram of wet E. coli cells. A sample of NEB#998 has been deposited under the terms and conditions of the Budapest Treaty with the American Type Culture Collection on Jul. 11, 1996 and received ATCC Accession Number 98102.

The following Example is given to illustrate embodiments of the present invention as it is presently preferred to practice. It will be understood that this Example is illustrative, and that the invention is not to be considered as restricted thereto except as indicated in the appended claims.

The references cited above and below are herein incorporated by reference.

EXAMPLE I

CLONING OF SapI RESTRICTION-MODIFICATION SYSTEM

1. Cloning of SapI Methylase Gene (M1).

10 μg of Saccharopolyspora sp. genomic DNA was cleaved partially by 4, 2, 1, 0.5, 0.25 units of Sau3AI at 37° C. for 30 min. The partilly digested DNA was analysed by gel electrophoresis. It was found that 1 unit and 0.5 unit of Sau3AI digestion gave rise to limited partial digestion. The partial digestion was repeated for 200 μg DNA (10 μg DNA in one tube, 20 digestions were performed). Genomic DNA fragments in the range of 2–20 kb were gel purified by excision of DNA from the agarose gel, freeze-thawing, and centrifugation. The supernatants containing DNA was precipitated with 95% ethanol. The pellet was washed with 70% ethanol, dried, and resuspended in TE buffer. The Sau3AI partially digested Saccharopolyspora sp. genomic DNA was ligated into BamHI cleaved/CIP treated pUC19 DNA at 16° C. onvernight. Ligated DNA was transformed into RR1 competent cells and plated on ampicillin plates. A total of about $5 \times 10^4$ cells were derived from the transformation. These cells were pooled together and inoculated into 1 liter LB broth plus Ap and cultured overnight at 37° C. Plasmid DNAs were prepared from the primary cell library. 10, 5, 2, 1 μg of plasmid DNA were cleaved with SapI restriction endonuclease for four hours at 37° C. The SapI-digested DNAs were retransformed into RR1 competent cells. Plasmid DNAs were isolated again from the surviving transformants and digested with SapI restriction enzyme to see if the plasmid DNA is resistant to SapI digestion. 72 plasmids were checked for resistance to SapI digestion. One resistant clone (#32) was found that carries about 1.5 kb genomic DNA insert. The entire insert was sequenced using deletion clones and primer walking with custom primers. It was found that the insert contains the SapI methylase gene (M1).

The predicted amino acid (aa) sequence contains conserved N$^4$ cytosine methylase motifs of VXDPXGGXGT (SEQ ID NO:4) and SPPF. The DNA coding sequence and predicted aa sequence are shown in FIG. 3.

2. Restriction Mapping of Genomic DNA Surrounding SapI M1 Gene.

One ClaI-SmaI DNA fragment encoding the C-terminus of M1 methylase from the M1 clone was used as a probe in the Southern blot to detect genomic DNA that had been digested by AatII, EcoO109I, EcoRI, KpnI, PvuI, SmaI, SphI, SspI, XbaI, XmnI, AflII, AvrII, BsgI, BspEI, BstBI, Bsu36I, DraIII, EagI, Eco47III, EcoNI, MscI, MunI, NcoI, NdeI, NruI, PflMI, PmlI, RsrII, SacII, SnaBI, SpeI, or StyI. The endonuclease digested genomic DNA was subjected to electrophoresis in a 0.8% agarose gel. The DNA was denatured and transferred to a nitrocellulose membrane by blotting. The DNA in the membrane was hybridized with biotinylated ClaI-SmaI fragment probe at 65° C. overnight. The hybridized DNA was detected by NEBlot® phototope detection system. (New England Biolabs, Inc. Beverly, Mass.) The same genomic DNA membrane was stripped and reprobed with a ClaI-SphI DNA probe coding for the N-terminus of SapI methylase M1. The Southern blots indicated that EcoRI (11 kb), KpnI (5.8 kb), and SmaI (6.5 kb) fragments were good candidates for cloning of surrounding DNA encoding SapI M2 gene and/or SapI retriction endonuclease gene.

3. Cloning of SapI Methylase Gene M2.

Saccharopolyspora sp. genomic DNA was cleaved with EcoRI, KpnI, or SmaI. The digested DNA was subjected to electrophoresis in a 0.8% agarose gel. EcoRI fragments about 11 kb, KpnI about 5.8 kb, and SmaI fragments about 6.5 kb were gel-purified and ligated into EcoRI, KpnI, and SmaI digested and CIP-treated pUC19 vector. The ligated DNA was transformed into RR1 competent cells. About 6,000 colonies were pooled together and inoculated into 500 ml LB broth plus Ap and cultured overnight. Plasmid DNAs were prepared from the mixed primary cell libraries. 10, 5, 2, 1 µg of plasmid DNA were cleaved with SapI restriction endonuclease for four hours at 37° C. The SapI-digested DNAs were retransformed into RR1 competent cells. The transformants were used for colony hybridization using M1 DNA probe. Plasmid DNAs were isolated from positive clones and digested with SapI restriction enzyme to see if the plasmid DNA is resistant to SapI digestion. Isolates #5, #18, and #32 were partially resistant to SapI digestion and contains the 5.8 kb KpnI genomic insert. Restriction mapping, deletion mapping, and DNA sequencing indicated that the insert carries a second methylase gene M2 and majority of M1. The coding sequence and predicted aa sequence of M2 is shown in FIG. 4. SapI M2 methylase also contains conserved N$^4$ cytosine methylase motifs: VXDPXGGXGT (SEQ ID NO:4) and SPPY. The extra DNA upstream of M2 is about 3.3 kb. The DNA adjacent to M2 was sequenced in the hope of finding open reading frames that might be SapI endonuclease gene. A total of 1731 bp of DNA was sequenced and this sequence was used to search homology to all known genes in GenBank. One open reading frame upstream of M2 was found to have similarity to a gene that is involved in antibiotics synthesis. It was concluded that this open reading frame upstream of M2 gene is not SapI restriction endonuclease gene.

4. Cloning of Part of SapI Restriction Endonuclease Gene by Construction Partial NlaIII Library.

Since the SapI endonuclease gene is most likely located downstream of M1 gene, we tried to clone larger DNA fragments carrying both M1 and SapI endonuclease gene. Saccharopolyspora sp. genomic DNA was partially digested with NlaIII restriction endonuclease. Genomic DNA fragments ranging from 3–20 kb were gel-purified and inserted into SphI-digested and CIP-treated pUC19. The ligated DNA was used to transform RR1 competent cells. Plasmid DNAs were prepared from the primary cell library. 10, 5, 2, 1 µg of plasmid DNA were cleaved with SapI restriction endonuclease for four hours at 37° C. The SapI-digested DNAs were retransformed into RR1 competent cells. Plasmid DNAs were isolated and digested with SapI restriction enzyme to see if the plasmid DNA is resistant to SapI digestion. After screening 153 plasmid isolates, pUC19-genomic inserts #9, #13, #14, #59, #83, #84, #88, #109, #118, #123, #126, #133, #148 were found to be resistant to SapI digestion. Restriction mapping indicated that #13, #14, and ##59 carry the same inserts and the DNA downstream of M1 methylase gene was sequenced. The insert of #13 contains extra DNA that extended the M1 insert further out 657 bp. But this 657 bp is not large enough to encode the entire SapI restriction endonclease gene. #13 did not displayed any detectable SapI restriction endonuclease activity in cell extract.

5. Cloning the Remainder of SapI Endonuclease Gene by Inverse PCR.

Inverse PCR was used to amplify DNA sequences that are downstream of M1 gene. Saccharopolyspora sp. genomic DNA was digested with AflIII, AgeI, AseI, BglII, BsaHI, BsrFI, BstYI, ClaI, EcoRI, KasI, KpnI, MluI, NgoMI, PaeR7I, Ppu10I, or PstI restriction enzymes. The digested DNAs were self-ligated at a low DNA concentration (ligation reaction: 20 µl of digested DNA, about 1 µg, 50 µl 10× ligation buffer, 5 µl of T4 DNA ligase, 425 µl of sterile distilled water, 16° C. overnight). The ligated circular DNA was purified by phenol-CHCl$_3$ extraction and ethanol precipitation and used as templates for inverse PCR reaction using a set of primers that annealed to the end of the SapI M1 gene. The primer sequences used in inverse PCR were:

forward primer: 5' TAAGCTATCTTGGTCAGTCAAAG 3' (SEQ ID NO:5)

reverse primer: 5' AACAGGAGATGATGTTTAGTTGTA 3' (SEQ ID NO: 6)

The inverse PCR reaction conditions were 95° C. for 1 min, 60° C. for 1 min, and 72° C. for 2 min, running 30 cycles. Inverse PCR products were found in AflIII, AgeI, AseI, BsaHI, BsrFI, BstYI, ClaI, KasI, MluI, PaeR7I, and Ppu10I digested and self-ligated DNA templates. The inverse PCR products from ClaI (1.4 kb) and NsiI (1.6 kb) reactions were treated with T4 polynucleotide kinase and T4 DNA polymerase and cloned into HincII-cleaved/CIP treated pUC19 vector. The entire inserts were sequenced using deletion clones and custom primers. One open reading frame was found that runs in the opposite direction as compared to M1 gene. The DNA coding sequence and the predicated aa sequence are shown FIG. 5.

6. Expression of SapI Endonuclease Gene in PUC19.

Figure 6:
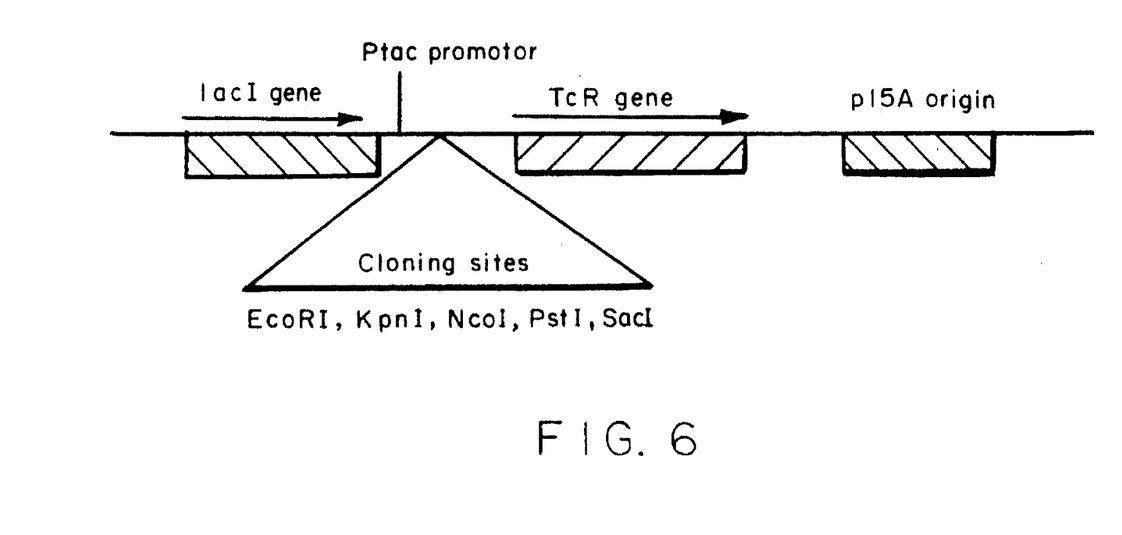

The SapI M1 gene was subloned into pR976 (Tc$^R$, a pACYC184 derivative, FIG. 6) and the M2 gene was cloned into pLG339 (Kn$^R$, a pSC101 derivative, Stoker et al., Gene 18:335–341). Both pR976-M1 and pLG339-M2 were transformed into E. coli to premodify host chromosome. The SapI endonuclease gene was amplified by PCR and ligated into pUC19. A low level of SapI expression was achieved in E. coli [pR976-M1, pLG339-M2, pUC19-SapIR], but the strain was not stable. SapI activity was detected only in 10 ml culture. SapI activity was lost in 500 ml culture.

7. Expression of SapI Endonuclease Gene in a Low Copy Number Plasmid pR976 Under P$_{tac}$ Promoter Control.

Since SapI expression in a high copy number plasmid such as pUC19 was not stable, it was thought that expression on a low copy number plasmid may stablize the expression. *E. coli* competent cell was transformed with pUC19-M1 and pLG339-M2 to modify the host DNA. SapI endonuclease gene was amplified by PCR and inserted into the PstI site of pR976. The strain *E. coli* [pUC19-M1, pLG339-M2, pR976-SapIR] produced about 1000 units of SapI per gram of wet *E. coli* cells, a 3-fold overproduction than the native strain. Again the strain was not stable because it reduced the activity in large cell culture. This instability was probably caused by the under-methylation and constitutive endonuclease expression from the $P_{tac}$ promotor.

8. Expression of M1 and M2 on DUC19 and pACYC184.

Because the SapI expression clone was not stable, it was thought that overexpression SapI methylase genes M1 and M2 may help to alleviate the problem. An efficient ribosome binding site GGAGGT and 6 bp spacing AAATAA were engineered in front of M2 gene by PCR and the gene was inserted into pUC19-SapIM1. The resulting plasmid was pUC19-SapIM1-M2 (there is one SapI site in the vector). When this plasmid was isolated and digested with SapI, only about 70% of DNA was resistant to SapI digestion, indicating poor SapI methylase expression/instability of SapI methylase proteins in vivo.

To compare the SapI methylase modification level in vivo, the M1 and M2 genes were also cloned into pACYC184. The resulting plasmid was pACYC184-SapIM1-M2. This plasmid and pUC19 was co-transformed into *E. coli* cells. Plasmid DNA mixture was isolated from the cells and subjected to SapI digestion (there is one SapI site in pUC19, no SapI site in pACYC184-SapIM1-M2). It was found that about 70% of pUC19 DNA was resistant to SapI digestion, indicating that the methylase expression from a high copy number plasmid and a low copy number plasmid resulted in the similar level of SapI site modification.

9. Expression of SapI Endonuclease Gene in a Modified T7 Expression Vector.

Two primers were made to amplify the SapI endonuclease gene. The primer sequences are:
forward primer:

5' CGCTCTAGA (XbaI site) GGAGGT (ribosome binding site) TAAATA (spacing) ATGCGGAGGCTTGC-TACACAACGACGC 3' (SEQ ID NO:7)

reverse primer:

5' GAGGGATCC (BamHI site) TCAGTCCAGTGG-TAGTGCTTCATC GAG 3' (SEQ ID NO:8).

The SapI endonuclease gene was amplified from Saccharopolyspora sp. genomic DNA with Taq DNA polymerase plus Vent® DNA polymerase (50:1 ratio) under the PCR condition 95° C., 1 min, 60° C., 1 min, 72° C., 1 min 30 sec for 20 cycles. The PCR DNA was purified by phenol-$CHCl_3$ extraction and ethanol precipitation and resuspended in TE buffer. The DNA was digested with BamHI and XbaI restriction endonucleases and ligated into a modified T7 expression vector pET21t. The expression vector pET21t contains transcription terminators upstream of the T7 promotor to further reduce the basal level of expression under non-induced condition (pET21t was constructed and provided by H. Kong, New England Biolabs, Inc., Beverly, Mass.). The ligated DNA was used to transform SapI methylase modified cell ER2504 [pACYC-SapIM1-M2]. ER2504 is a BL21($\lambda$DE3) derivative that is also TonA⁻ and DNasI⁻. *E. coli* cells ER2504 [pACYC-SapIM1-M2, pET21t-SapIR] were grown in LB broth to late log phase (about 150 klett units) and IPTG was added to a final concentration of 0.5 mM to induce endonuclease production. IPTG-induction and cell culture continued for 3 hours. Cells were harvested by centrifugation and resuspended in sonication buffer (10 mM β-mercaptoethanol, 50 mM Tris-HCl pH 7.5). Cells were lysed by addition of lysozyme and sonication. Cell debris was removed by centrifugation and the supernatant was assayed for SapI activity on λDNA. The strain produced about 20,000 units of SapI restriction endonuclease per gram of wet *E. coli* cells. It still produces SapI endonuclease in cells cultured in a 100 liter fermentor.

10. Purification of Recombinant SapI Restriction Endonuclease.

The recombinant SapI restriction endonuclease was purified by chromatography through Heparin-Sepharose column, phosphocellulose column, and Q-Separose HPLC. The purified enzyme was assayed on λ DNA and pUC19 substrate.

What is claimed is:

1. Isolated DNA coding for the SapI restriction endonuclease, wherein the isolated DNA is obtainable from Saccharopolyspora sp.

2. A recombinant DNA vector comprising a vector into which a DNA segment coding for the SapI restriction endonuclease has been inserted.

3. Isolated DNA coding for the SapI restriction endonuclease and methylase, wherein the isolated DNA is obtainable from ATCC No. 98102.

4. A cloning vector which comprises the isolated DNA of claim 3.

5. A host cell transformed by the cloning vector of claims 2 or 4.

6. A method of producing a SapI restriction endonuclease comprising culturing a host cell transformed with the vector of claim 2 or 4 under conditions suitable for expression of said endonuclease.

* * * * *

UNITED STATES PATENT AND TRADEMARK OFFICE
CERTIFICATE OF CORRECTION

PATENT NO. : 5,663,067

DATED : September 2, 1997

INVENTOR(S) : Xu, et al

It is certified that error appears in the above-indentified patent and that said Letters Patent is hereby corrected as shown below:

Column 2, line 57, replace "cytostne" with --cystosine--

Column 5, line 7, replace "closed" with --cloned--

Column 5, line 14, replace "Clai-SphI" with
   --*Cla*I-*Sph*I--

Column 5, line 17, replace "BstBi" with --*Bst*BI--

Column 5, line 18, replace "MscI, SnaBI" with
   --MscI, MunI, NcoI, NdeI, NruI, Pf1MI, PmlI, RsrII, SacII--

Column 5, line 21, replace "clonging" with --cloning--

UNITED STATES PATENT AND TRADEMARK OFFICE
CERTIFICATE OF CORRECTION

PATENT NO. : 5,663,067
DATED : September 2, 1997
INVENTOR(S) : Xu, et al

It is certified that error appears in the above-indentified patent and that said Letters Patent is hereby corrected as shown below:

Column 4, line 3, replace "stabalize" with --stabilize--.

Column 6, line 51, replace "onvernight" with --overnight--

Column 9, line 3, replace "stablize" with --stabilize--.

Signed and Sealed this

Fourteenth Day of July, 1998

Attest:

BRUCE LEHMAN

*Attesting Officer*   *Commissioner of Patents and Trademarks*